June 3, 1941. E. BECKETT Plant Pat. 472
CLEMATIS
Filed June 20, 1939
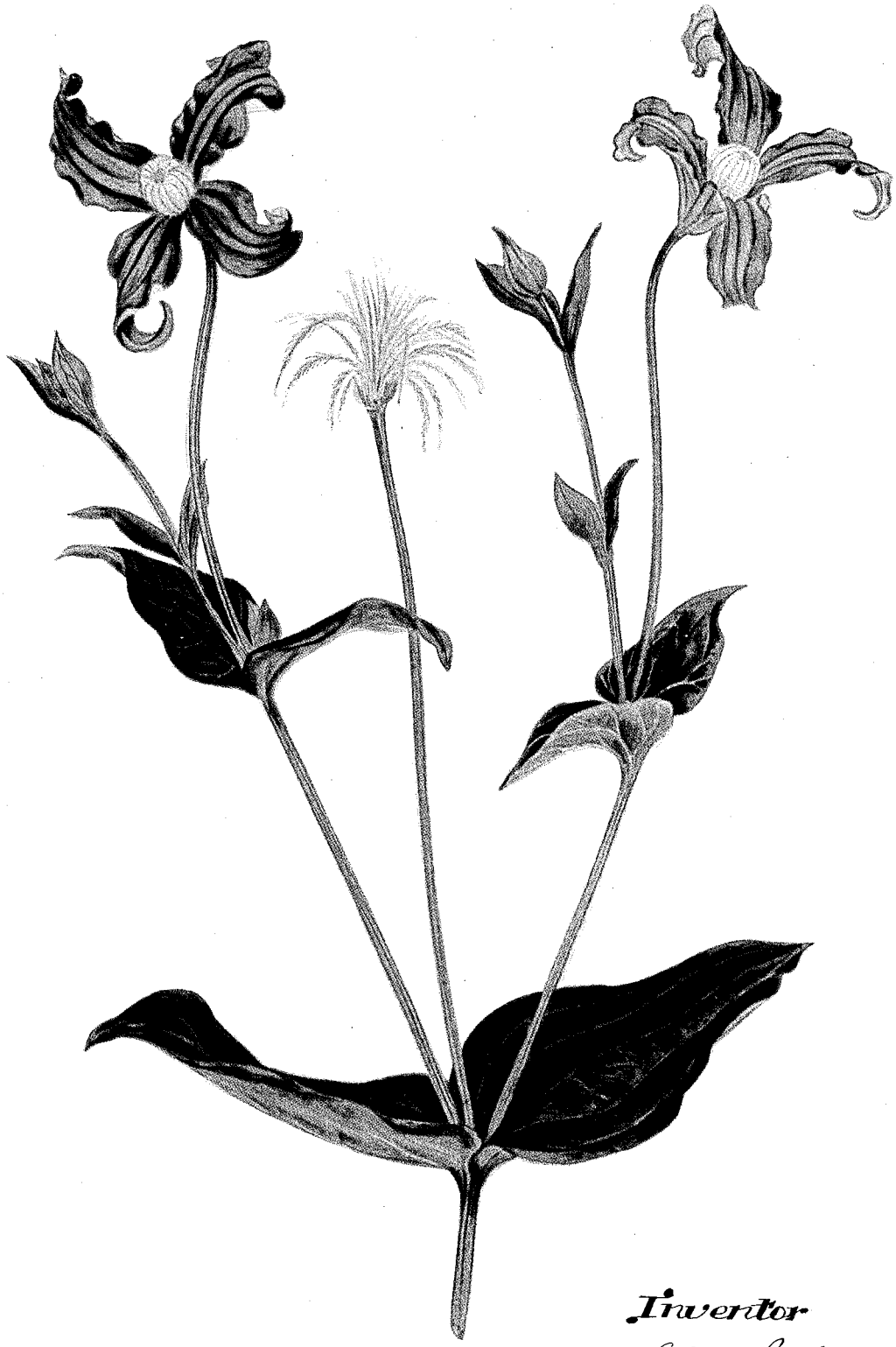
Inventor
Edwin Beckett
By Cecil B. Rice
Atty.

Patented June 3, 1941

Plant Pat. 472

UNITED STATES PATENT OFFICE

472

CLEMATIS

Edwin Beckett, Red Bank, N. J.

Application June 20, 1939, Serial No. 280,074

1 Claim. (Cl. 47—60)

This invention relates to a new hybrid clematis of the herbaceous non-climbing type, developed by me as a result of crossing one of the hybrid climbing varieties with *Clematis integrifolia*, a non-climbing species.

The resulting new variety, which is described more fully below, and illustrated by the accompanying painting, is an herbaceous plant and has the bush like habit which characterizes the *integrifolia* species used as a parent, but while about of the same general height is more spreading in character. It differs from *Clematis integrifolia* in that it is more floriferous, the flowers are larger, almost erect as opposed to the somewhat nodding flowers of *integrifolia*, its blooming season is over a longer period, lasting from June to late August. The first crop of flowers is followed by a more or less scattered crop throughout the summer, but if the plant is pruned back lightly after the first burst of bloom another crop of flowers, equal in profusion to the first, is borne in August. It differs from the parent of climbing habit in that it is strictly herbaceous in character, non-climbing and the flowers are somewhat smaller. Being a hybrid it does not reproduce true from seed, applicant's stock having been propagated asexually from the original plant.

*Description*

Parentage: *Seed parent.*—Hybrid clematis of the *lanuginosa* section. *Pollen parent.*—*Clematis integrifolia.*

Plant: Hardy herbaceous perennial, stems up to two feet in height, always erect or ascending, stems angled covered with very short downy hair, leafy from the ground up. The stems are parrot green, Ridgway color chart Plate VI, color 31, Y-G, line K. The ridges of the stems are sepia, Ridgway color chart plate XXIX, color 17, O-Y, line M. Very hardy, having withstood sub-zero temperature without protection.

Leaves: Sessile or nearly so, palmately veined from the base, ovate, margin is entire and densely downy, the blade of the leaf smooth on both surfaces, the lower surface reticulate, measuring up to four inches in length. The upper surface of the leaves is cedar green, Ridgway chart Plate VI, color 31, Y-G, line M. The lower surface of the leaves is grass green, Ridgway color chart, Plate VI, color 33, GY-G, line K. Leaf tips short acuminate.

Flower: The first flower is terminal and pediceled. From the axils of the subtending leaves branches arise each bearing a terminal pediceled flower. This branching continues somewhat intermittently through the flowering season if the plant is left untouched. A good second crop of flowers is produced, if the plant is pruned slightly, during August. The flower is peduncled, erect, sepals four, sepals one and one quarter to one and one-half inches long, one-half to three-quarters of an inch broad, narrow elliptic. Margin undulate and somewhat crisped. The margin irregularly and minutely crenulate, the tip short acuminate. The upper surface is smooth, the central portion with two to four convex ridges. The under surface has four strong ridges corresponding with the grooves between the upper ridges. Tips acuminate.

The color of the inner surface of the petals is deep soft blue violet (Ridgway Plate XXIII) (2), outer surface dull bluish-violet (Ridgway Plate XXXIV) (2). Veins dark dull bluish-violet (Ridgway Plate XXXIV).

Stamens numerous, the outer series one-half to five-eighths of an inch, inner series somewhat shorter. The filaments are greenish-cream colored, finely pubescent, narrowly linear spatulate tapering again towards the apex. The apical eighth of an inch is a dull lemon-yellow, silkily pubescent on the outer side with the two anther sacs sessile on the inner side. The pistils are close together, in a narrow, ovoid, conical head the same length as the stamens, the capillary blade closely covered with long silky hairs, the styles shortly curved, nearly naked. Usually sterile.

I claim:

The new and distinct variety of clematis substantially as shown and described characterized by the color of flower and vegetative parts.

EDWIN BECKETT.